United States Patent
Li et al.

(10) Patent No.: US 10,504,229 B2
(45) Date of Patent: Dec. 10, 2019

(54) MEDICAL IMAGE PROCESSING APPARATUS AND MEDICAL IMAGE PROCESSING METHOD

(71) Applicant: Toshiba Medical Systems Corporation, Otawara-shi (JP)

(72) Inventors: Bing Li, Beijing (CN); Xiaowei Yuan, Beijing (CN); Jinbiao Zhang, Beijing (CN); Jing Liu, Beijing (CN)

(73) Assignee: Canon Medical Systems Corporation, Otawara-shi (JP)

( * ) Notice: Subject to any disclaimer, the term of this patent is extended or adjusted under 35 U.S.C. 154(b) by 81 days.

(21) Appl. No.: 15/642,741

(22) Filed: Jul. 6, 2017

(65) Prior Publication Data

US 2018/0122074 A1    May 3, 2018

(30) Foreign Application Priority Data

Oct. 28, 2016 (CN) .......................... 2016 1 0961249
May 10, 2017 (JP) ................................ 2017-094113

(51) Int. Cl.
| | | |
|---|---|---|
| G06K 9/00 | (2006.01) | |
| G06T 7/00 | (2017.01) | |
| A61B 5/00 | (2006.01) | |
| G06T 7/73 | (2017.01) | |

(52) U.S. Cl.
CPC .......... *G06T 7/0014* (2013.01); *A61B 5/4041* (2013.01); *A61B 5/4064* (2013.01); *A61B 5/7425* (2013.01); *A61B 2576/026* (2013.01); *G06T 7/73* (2017.01); *G06T 2207/30016* (2013.01); *G06T 2207/30096* (2013.01)

(58) Field of Classification Search
CPC ..................... G06T 7/0014; G06T 7/73; G06T 2207/30016; G06T 2207/30096; A61B 5/4041; A61B 5/4064; A61B 5/7425; A61B 2576/026

See application file for complete search history.

(56) References Cited

U.S. PATENT DOCUMENTS

| | | | | |
|---|---|---|---|---|
| 6,272,370 | B1 * | 8/2001 | Gillies .............. | A61M 25/0105 324/309 |
| 7,634,317 | B2 * | 12/2009 | Ben-David ............ | A61B 5/412 607/14 |

(Continued)

FOREIGN PATENT DOCUMENTS

| | | |
|---|---|---|
| JP | 2012-66005 | 4/2012 |
| JP | 2012-235934 | 12/2012 |

OTHER PUBLICATIONS

El Jundi, B., and S. Heinze. "Three-dimensional atlases of insect brains." Neurohistology and Imaging: Basic Techniques (2016).*

*Primary Examiner* — Shefali D Goradia
(74) *Attorney, Agent, or Firm* — Oblon, McClelland, Maier & Neustadt, L.L.P.

(57) ABSTRACT

A medical image processing apparatus according to an embodiment includes processing circuitry configured to: extract position information of innervation from subject data; convert a subject nerve region that is based on the extracted position information into atlas data; analyze a position relation between a functional area in a brain in the atlas data and the converted subject nerve region; and convert the analysis result into the subject data.

16 Claims, 13 Drawing Sheets

(56) References Cited

U.S. PATENT DOCUMENTS

| | | | | |
|---|---|---|---|---|
| 7,834,627 | B2* | 11/2010 | Sakai | G01R 33/56341 324/307 |
| 8,090,164 | B2* | 1/2012 | Bullitt | G06T 7/0014 382/128 |
| 8,559,686 | B2* | 10/2013 | Azemoto | G06T 7/32 382/128 |
| 2004/0096089 | A1* | 5/2004 | Borsook | A61B 5/055 382/131 |
| 2011/0069873 | A1* | 3/2011 | Azemoto | G06T 7/32 382/128 |
| 2012/0065494 | A1* | 3/2012 | Gertner | A61B 5/055 600/411 |
| 2015/0078642 | A1* | 3/2015 | Fang | A61B 5/14553 382/131 |
| 2017/0177812 | A1* | 6/2017 | Sjolund | A61N 5/103 |
| 2018/0164879 | A1* | 6/2018 | Moffat | G06F 3/017 |

* cited by examiner

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from Chinese Patent Application No. 201610961249.8, filed on Oct. 28, 2016; and Japanese Patent Application No. 2017-94113, filed on May 10, 2017, the entire contents of which are incorporated herein by reference.

FIELD

Embodiments described herein relate generally to a medical image processing apparatus and a medical image processing method.

BACKGROUND

Recently, with the development of the image recognition techniques, there is an increasing interest in the techniques for analyzing the position relation between nerve fiber bundles and lesions imaged in medical images.

Many brain diseases will affect the deformation of the white matter fiber, e.g., may cause deformations such as blocked, infiltration or extrusion. Knowledge of these changing can provide a neurosurgery with useful information. In particular, with respect to the situation of infiltration, the excision extent is closely related to the prognosis. In fact, highly invasive lesions will largely change the morphology, and will harm the function of the infiltrated white matter fiber, but low invasive tumors may only extrude the surrounding brain tissues. These different situations will affect the formulation of the surgery strategy. Therefore, by accurately determining the position relation between white matter fibers of different functions and the lesions, it can help to find an optimal compromise between the excision extent of tissues and retaining the brain functions as far as possible.

When a physician makes a plan for a tumor surgery, it is needed to discriminate the functions of associated nerve fiber bundles. Tracking of the nerve fiber bundles can provide such information.

In prior arts, methods of discriminating the function of nerve fiber bundles have disclosed. A method of discriminating nerve fiber bundle functions is disclosed in prior art, e.g., in patent document 1, it disclosed first determining the nerve fiber bundles that traverse a lesion, and then determining the arrival points in the brain region of the nerve fiber bundles that traverse the lesion, utilizing a template of cerebral cortex functional area to determine the functional area of the cerebral cortex that is in connection with the arrival points of the nerve fiber bundles, thereby predicting possible influences to the subject.

However, this analysis method can be only used to detect the affected fiber bundles that traverse the lesion, and cannot detect the affected fiber bundles that are extruded but do not traverse the lesion. Furthermore, utilizing this analysis method can only demonstrate the connection between the fiber bundles and the cerebral cortex functional areas and predict the functional categories of the affected fiber bundles, but cannot extract and display the actual morphology and position of the affected fiber bundles.

Moreover, prior document 2 discloses a method of extracting nerve fiber bundles, which conducts a logical calculation between a set of nerve fiber bundles extracted by a nerve fiber bundle tracker and a set of nerve fiber bundles selected based on the region of interest (ROI, sometimes referred as "seed region") of the nerve fiber bundles, so as to determine a set of certain nerve fiber bundles. This set is a set of fiber bundles that traverse a certain region of interest and exceed a threshold in terms of anisotropy, but the set of these fiber bundles is only correlated in position and is not correlated in function, and it is thus unable to obtain the functional categories of the fiber bundles while extracting the fiber bundles.

Moreover, in prior arts, it is generally to obtain the region of interest from the result of blood oxygen level dependent functional magnetic resonance imaging (BOLD-fMRI) and thereby to track the fiber bundles. This does not only need to obtain the result of blood oxygen level dependent functional magnetic resonance imaging, but is also not easy to obtain high quality result of blood oxygen level dependent functional magnetic resonance imaging in practice.

DETAILED DESCRIPTION

A medical image processing apparatus comprises processing circuitry. The processing circuitry is configured to extract position information of innervation from subject data. And the processing circuitry is configured to convert a subject nerve region that is based on the extracted position information into atlas data. And the processing circuitry is configured to analyze a position relation between a functional area in a brain in the atlas data and the converted subject nerve region. And the processing circuitry is configured to convert the analysis result into the subject data.

Embodiments described herein relate generally to the medical image processing apparatus for processing medical images. The medical image processing apparatus can be implemented by executing software relating to respective functions of the medical image processing apparatus with a device having CPU (Central Processing Unit), such as an independent computer connected to an imaging acquisition apparatus of an X-ray apparatus etc., and can also be implemented by way of hardware by circuitry that can perform respective functions of the medical image processing apparatus. Also, the medical image processing apparatus of the embodiments can also be pre-installed in the image acquisition apparatus as a part of the medical image acquisition apparatus such as a CT apparatus or an ultrasound imaging apparatus.

In the following, the embodiments will be described in detail in connection with the drawings. The embodiments have been presented by way of example only. The Following description are not intended to limit the embodiments.

The following description will be made by taking a brain region as an exemplary example, however, the embodiments are not limited to the brain region, but can be also applied to image processing on other regions.

First Embodiment

Figure 1:
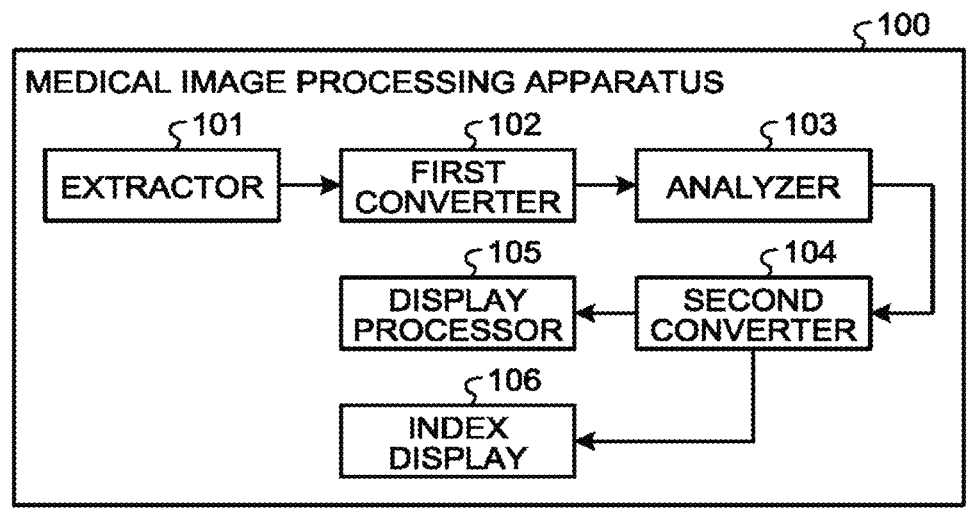
FIG. 1 is a block diagram representing a medical image processing apparatus according to a first embodiment.

FIG. 1 is a block diagram representing a medical image processing apparatus according to a first embodiment.

As illustrated in FIG. 1, a medical image processing apparatus 100 comprises: an extractor 101, a first converter 102, an analyzer 103, a second converter 104, a display processor 105, and an index display 106.

The extractor 101 extracts position information of innervation from subject data. The subject data includes a fiber bundle image. The fiber bundle image is a nerve fiber image that is related to a nerve fiber bundle of a brain of a subject. The fiber bundle image is e.g., generated by applying a fiber bundle tracking technique to the diffusion tensor image generated after imaging the brain of the subject. The diffusion tensor imaging technique can evaluate the integrity of the white matter fiber bundle by imaging the diffusion characteristics of water molecules. Currently, the diffusion tensor imaging and the fiber bundle tracking techniques are used for the display of particular fiber bundles in vivo.

The first converter 102 can convert the fiber bundle image in the subject data into a predefined fiber bundle atlas. In other words, the first converter 102 converts the subject nerve region that is based on the position information of the innervation extracted from the fiber bundle image into the fiber bundle atlas (atlas data).

The predefined information in the fiber bundle atlas includes standardized information of the nerve regions and information of the functional areas that establish correspondences with nerve regions respectively. Wherein the nerve regions are regions corresponding to the nerve fiber bundles, and the function regions can also be referred to as regions of interest, which are regions corresponding to the brain functions (e.g., vision functional area, motion functional area etc. on the cerebral cortex) or regions corresponding to the tissue structures in the brain (e.g., internal capsule, cerebral peduncle etc.). The functional areas can either be manually selected by an operator or automatically selected by an instrument. The correspondence between the nerve regions and the functional areas in the fiber bundle atlas will be described hereinafter.

Figure 2:
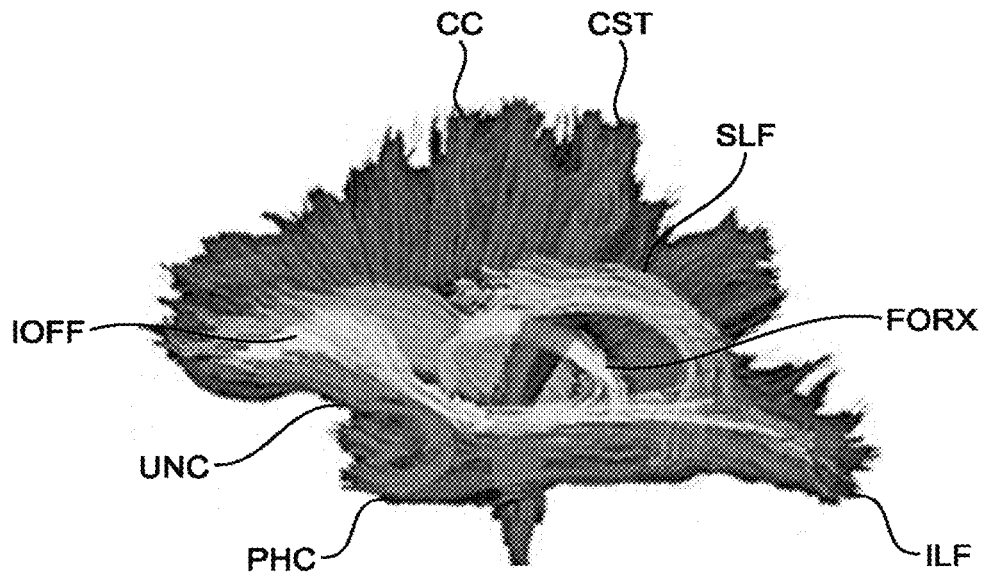
FIG. 2 is a view representing the functional fiber bundles included in the fiber bundle atlas.

The nerve fiber bundles in this embodiment refer to the fiber bundles labeled by the functional categories of the fiber bundles, i.e., functional fiber bundles. FIG. 2 is a schematic view representing the functional fiber bundles predefined in the fiber bundle atlas. FIG. 2 illustrates the functional fiber bundles including corpus callosum ("CC") that connects the left and right cerebral hemisphere, the cortico spinal tract ("CST") that connects the motion cortex and the spinal cord, the superior longitudinal fasciculus ("SLF") that connects the motion cortex and the spinal cord, the fornix ("FORX") that connects the hippocampus and the hypothalamic nucleus, the inferior longitudinal fasciculus ("ILF"), the parahippocampal cingulum or ("PHC"), the uncinate fasciculus ("UNC"), and the inferior occipitofrontal fasciculus ("IOFF" or "IFOF"), etc.

Furthermore, the fiber bundle atlas should be prepared before the conversion of the first converter 102 starts. This fiber bundle atlas can be an atlas that is predefined and stored in the extractor 101, an atlas that is imported into the medical image processing apparatus before the conversion of the first converter 102 starts, or an atlas that is generated by the medical image processing apparatus according to the embodiment.

In addition, in the process of converting the fiber bundle image from the subject into the fiber bundle atlas, the first converter 102, with respect to the fiber bundle image from the subject, generally converts it into the fiber bundle atlas by way of image registration (hereinafter referred to as "registration" for simplification). Specifically, with the existing registration methods, the image registration (hereinafter referred to as "registration" for simplification) is performed on the fiber bundle image from the subject and the images in the fiber bundle atlas, as a result of the image registration, a conversion matrix between the fiber bundle image of the subject and the fiber bundle atlas is generated, and a part or all of the fiber bundle image of the subject are converted into the predefined fiber bundle atlas.

The analyzer 103 analyzes the position relation between the functional areas in the brain in the fiber bundle atlas and the subject nerve fiber bundles converted into the fiber bundle atlas (that is, the converted subject nerve region).

Specifically, respective functional fiber bundles of the subject converted into the fiber bundle atlas are determined (identified) based on the conversion matrix, and then, based on the correspondence between the functional fiber bundles defined in the fiber bundle atlas and the regions of interest, as a result of the analysis, the regions of interest corresponding to the determined functional fiber bundles of the subject are obtained.

The second converter 104 converts the analysis result of the analyzer 103 into the subject data. For example, the second converter 104 converts the regions of interest obtained by the analyzer 103 into the subject data. Specifically, with the previously generated conversion matrix, the regions of interest obtained by the analyzer 103 are converted into the image of the subject data.

The display processor 105 causes the display apparatus (e.g., display etc.) to simultaneously display the fiber bundle image of the subject and the regions of interest corresponding to respective fiber bundles. Also, preferably, the regions of interest corresponding to different functional fiber bundles are represented with different colors or different grayscales, and thereby the operator can understand the function division of the regions of interest more intuitively.

Furthermore, with the fiber bundle tracking technique, the display processor 105 can also discriminate the functional fiber bundles in the subject data based on the regions of interest corresponding to functional fiber bundles. When displaying the fiber bundle image of the subject, the functional fiber bundles and the corresponding regions of interest are preferably represented with different colors or different grayscales, and thereby the operator can understand the function division of fiber bundles more intuitively.

However, for the medical image processing apparatus 100, the display processor 105 is not necessary. The display processor 105 may be disposed in other external apparatuses other than the medical image processing apparatus 100. It is even possible to output the processing result of the medical image processing apparatus 100 in other ways, without displaying.

In the following, the correspondence between nerve regions and functional areas in the fiber bundle atlas will be described with reference to FIG. 3 and FIG. 4.

Figure 3:
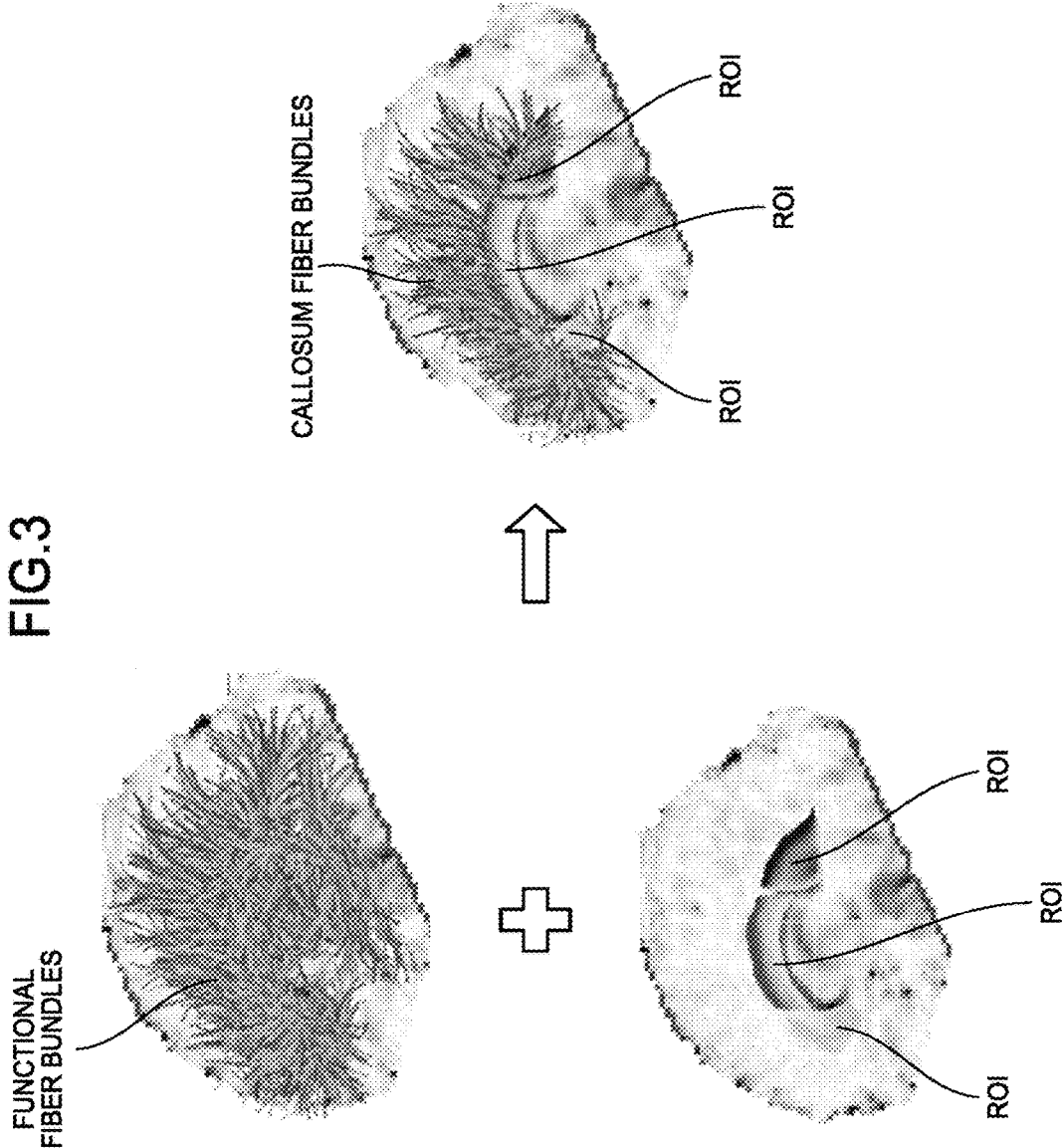
FIG. 3 is a schematic view representing the correspondence between the callosum fiber bundles and the region of interest in the fiber bundle atlas.

FIG. 3 is a schematic view representing the correspondence between the callosum fiber bundles and the region of interest in the fiber bundle atlas. In the upper left of FIG. 3, multiple functional fiber bundles predefined in the atlas are illustrated. In the lower left of FIG. 3, three regions of interest corresponding to the callosum fiber bundle on particular anatomy positions are illustrated. In the right of FIG. 3, a morphology that simultaneously displays the callosum fiber bundles and the three regions of interest are illustrated. There are three regions of interest for determining the callosum in FIG. 3, there is a logic "or" relation among these three regions of interest, i.e., a fiber bundles that traverses any one of the three regions of interest are determined as a callosum fiber bundles.

Figure 4:
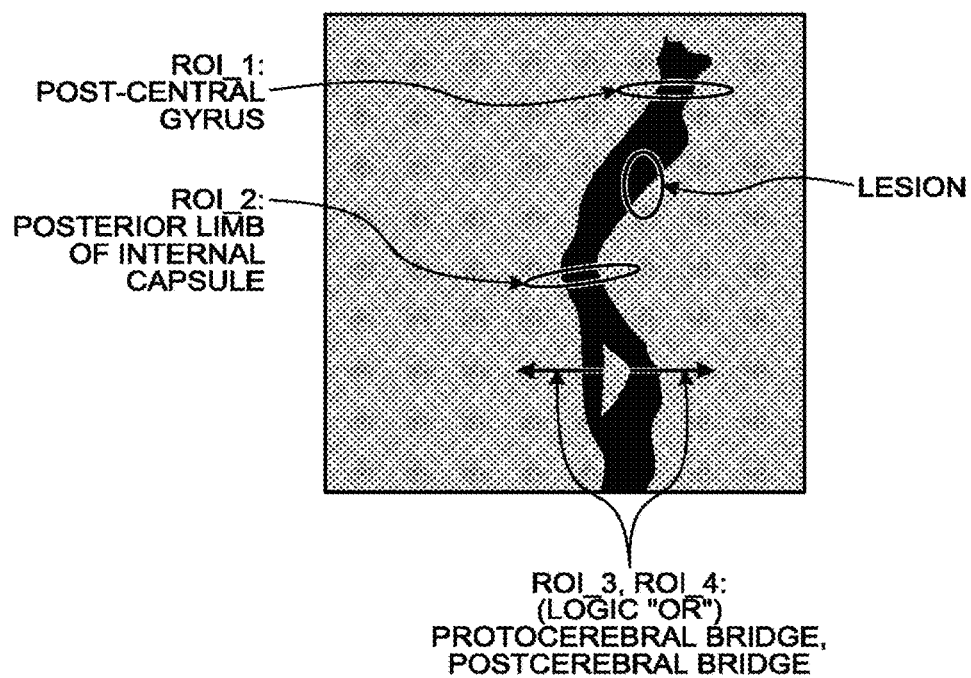
FIG. 4 is a schematic view representing the correspondence between the cortex spinal cord bundle and the region of interest in the fiber bundle atlas.

FIG. 4 is a schematic view representing the correspondence between the cortex spinal cord bundles and the regions of interest. The cortex spinal cord bundles and four regions of interest for determining the cortex spinal cord bundles are illustrated in the figures. It can be seen from this figure that, the cortex spinal cord bundles all traverse the region of interest 1 (post-central gyrus) and the region of interest 2 (posterior limb of internal capsule), while in regions of interest 3, 4, the cortex spinal cord bundles divides into two bundles, which traverse the region of interest 3 (protocerebral bridge) and the region of interest 4 (postcerebral bridge) respectively. Therefore, the logical relation between the several regions of interest for determining the cortex spinal cord bundle is: SD1 & SD2 & (SD3 or SD4), wherein SD represents the region of interest. In other words, functional fiber bundles traversing SD1 and SD2 and traversing SD3 or SD4 can be specified as cortex spinal cord bundles. For example, the lesion in FIG. 4 is tumor or the like.

FIG. 3 and FIG. 4 illustrate the method for determining respective regions of interest of the callosum fiber bundles and the cortex spinal cord bundles, and the logical relation between the regions of interest, however, in addition to the callosum fiber bundle, the cortex spinal cord bundle, there are also other functional fiber bundles in the brain, and the regions of interest for uniquely determining these functional fiber bundles and the logical relation between the regions of interest are defined respectively in the atlas. The number of regions of interest of respective functional fiber bundles and the logical relation between the regions of interest are different.

Figure 5:
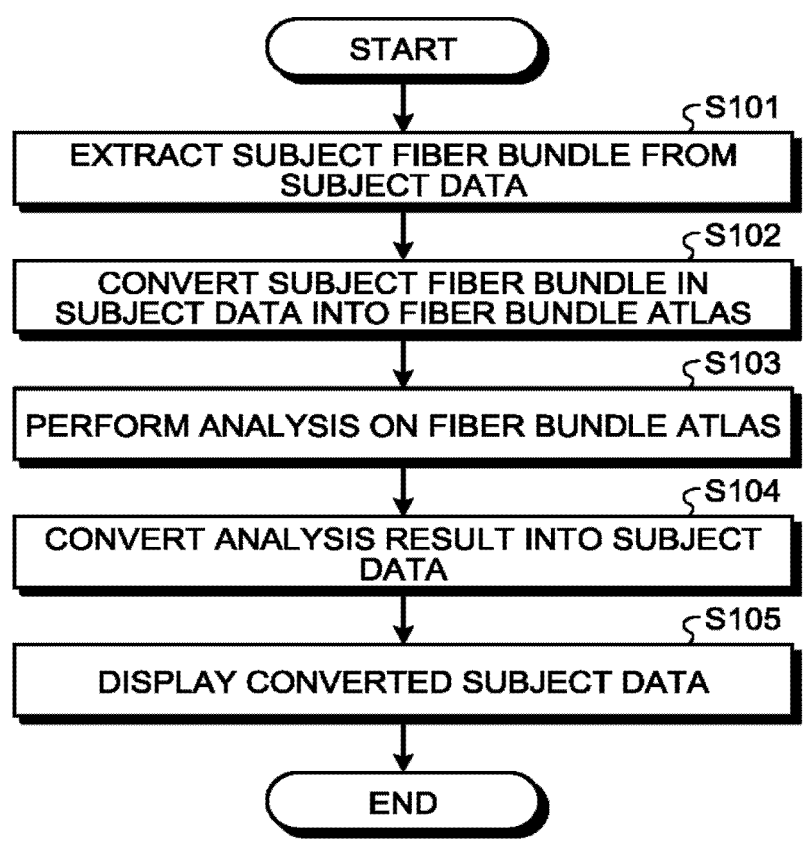
FIG. 5 is a flow chart of the image processing steps according to the first embodiment.
Figure 6:
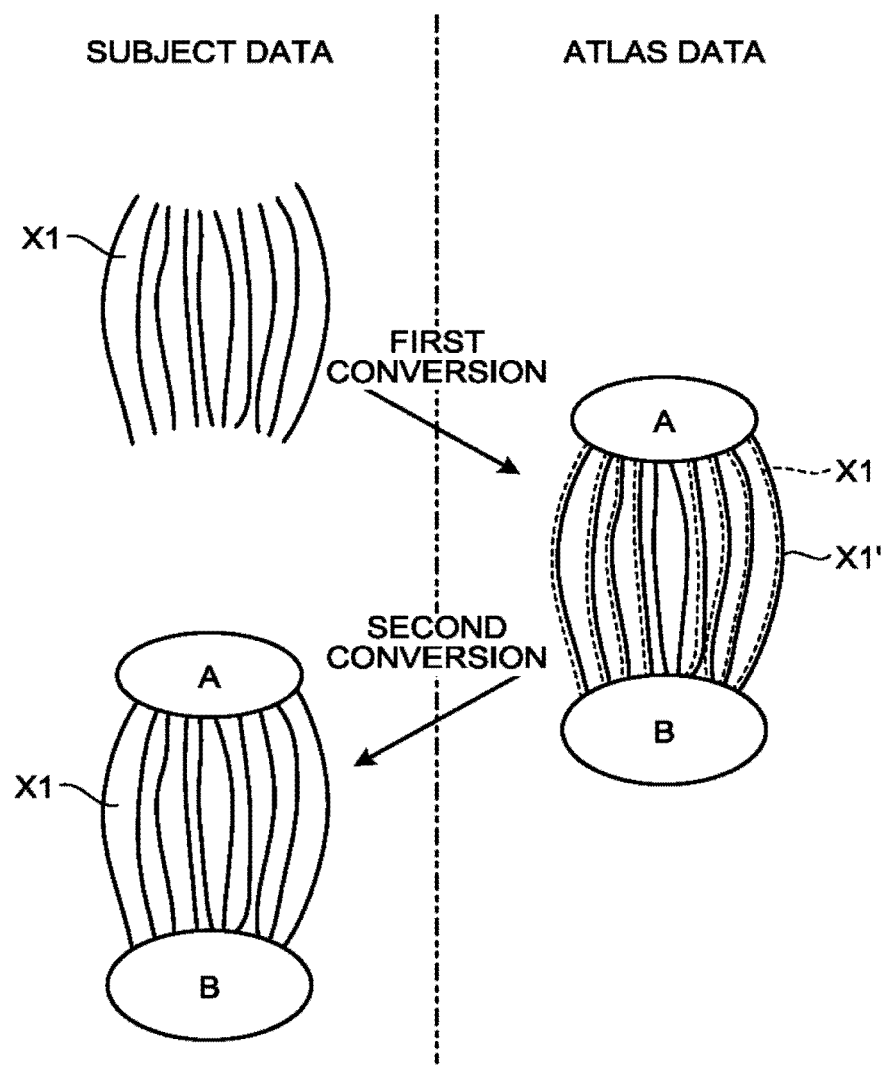
FIG. 6 is a schematic view representing the image processing according to the first embodiment.

In the following, the image processing process according to the first embodiment is described with reference to FIG. 5 and FIG. 6. FIG. 5 is a flow chart of the image processing steps according to the first embodiment. FIG. 6 is a schematic view representing the image processing according to the first embodiment.

The actual subject data includes multiple subject fiber bundles therein, however, for simplification of the description, FIG. 6 only schematically illustrates the image processing process of one nerve fiber bundle. Furthermore, the actual image processing may be a process conducted on a three dimensional image, however, for simplification of the description, description is made only by way of two dimensional planar image.

First, in step S101, the extractor 101 extracts the position information of the subject fiber bundle X1 from the subject data. The position information consists of coordinate information of multiple points on the three dimensional nerve fiber bundles, the density and quantity of the points can be set by the operator as needed. The upper left of FIG. 6 illustrates the subject fiber bundle X1, the position information of which is extracted, the subject fiber bundle X1 consists of eight nerve fibers.

The subject data can be pre-stored on a storage or an external storage device, also, the brain of the subject can be imaged by a medical image acquiring apparatus, the subject data including the fiber bundle image related to the nerve fiber bundles of the brain of the subject can be obtained using the fiber bundle tracking technique and the medical image diagnosis technique etc.

Next, in step S102, the first converter 102 converts the subject fiber bundle X1 that is based on the extracted position information into the fiber bundle atlas (atlas data).

Before the conversion, the fiber bundle atlas in the right of FIG. 6 includes the fiber bundle X1', and further includes a region of interest A and a region of interest B corresponding this fiber bundle X1'. The fiber bundle X1 constitutes of 10 nerve fibers connecting between the region of interest A and the region of interest B.

With respect to the generation of the fiber bundle atlas (i.e., with respect to the determination of the region of interest, the determination of the logical relation between multiple regions of interest, and the determination of the functional fiber bundles), it can be finished as long as before the first converter 102 conducts the conversion, it can either before the step S101 or after the step S101. Of course, a template of the fiber bundle atlas can be generated in advance and then stored on a storage or an external storage device, and this template can be invoked each time it is used.

Furthermore, in step S102, a conversion matrix obtained by registration can be used to convert the subject fiber bundle X1 from the subject into the fiber bundle atlas. In FIG. 6, the fiber bundle X1' predefined in the fiber bundle atlas is represented by solid lines, and the subject fiber bundle X1 converted into the fiber bundle atlas is represented by dashed lines.

Next, in step S103, an analyzer 103 analyzes the position relation between the region of interest A, the region of interest B in the fiber bundle atlas and the subject fiber bundle X1 converted into the fiber bundle atlas. The correspondence between the fiber bundle X1' and the region of interest A and the region of interest B is predefined in the fiber bundle atlas, i.e., fiber bundle X1' is a fiber bundle that connects between the region of interest A and the region of interest B. Thereby, as the analysis result, the region of interest A and the region of interest B corresponding to the subject fiber bundle X1 are obtained.

Next, in step S104, the second converter 104 converts the analysis result of the analyzer 103 into the subject data. That is, as illustrated in the lower left part of FIG. 6, the region of interest A and the region of interest B corresponding to the subject fiber bundle X1 are converted into the subject data.

Next, in step S105, the display processor 105 displays the subject data including the region of interest A and the region of interest B. Of course, for the medical image processing apparatus that only processes medical images, the step S105 related to the display can be omitted.

Processing finished.

By the image processing according to the first embodiment, a region of interest corresponding to the subject fiber bundles can be obtained from the fiber bundle atlas without using the result of blood oxygen level dependent functional magnetic resonance imaging. Furthermore, the region of interest in the fiber bundle atlas is predefined standardized data, and compared to the case that it is difficult to obtain high quality result of the blood oxygenation level dependent-functional magnetic resonance imaging in practice, the reliability of the region of interest obtained by the present embodiment is higher.

Furthermore, the first converter 102 in the first embodiment may also only perform image registration, and does not convert the fiber bundle image in the subject data into the predefined fiber bundle atlas. This is because that, even though the fiber bundle image in the subject data is not converted into the predefined fiber bundle atlas, the functional fiber bundles of the subject corresponding to the functional fiber bundles in the fiber bundle atlas may also be determined (identified) using the conversion matrix of the image registration.

The index display 106 of the first embodiment calculates and displays a damage index caused by the tumor region for the subject fiber bundles (subject nerve region) in the subject data. In the following description, this point is described with reference to FIG. 6.

For example, after the first converter 102 converts the subject nerve region in the subject data into the fiber bundle atlas, the analyzer 103 analyzes the position relation between the region of interest in the fiber bundle atlas and the subject nerve region converted into the fiber bundle atlas. For example, as illustrated in the right diagram in FIG. 6, the analyzer 103 analyzes the position relation between the region of interest A, the region of interest B in the fiber bundle atlas and the converted subject fiber bundle X1, and thus obtains the region of interest A and the region of interest B corresponding to the converted subject fiber bundle X1, as the analysis result. Furthermore, the analyzer 103 obtains the nerve region in association with the obtained functional area based on the correspondence of the regions of interest and the nerve regions having been defined in the fiber bundle atlas. For example, the analyzer 103 obtains a fiber bundle X1' as a nerve region that has established a correspondence with the region of interest A and the region of interest B that are obtained based on the position relation to the subject fiber bundle X1.

Next, the index display 106 compares the subject nerve region converted into the fiber bundle atlas with the nerve region obtained by the analyzer 103 to calculate the damage index. For example, the index display 106 compares the subject fiber bundle X1 converted into the fiber bundle atlas with the fiber bundle X1' obtained by the analyzer 103 to calculate statistical information of the subject nerve region as the damage index.

For example, the statistical information of the subject nerve region calculated by the index display 106 is represented by a functional rate representing the ratio of the functional fiber bundles that are usable before the surgery to the functional fiber bundles related to the regions of interest (for example, the functional fiber bundles that are usable when the subject data is obtained). As an example, in the atlas data illustrated in FIG. 6, the fiber bundle X1' related to the region of interest A and the region of interest B consists of 10 nerve fibers and the subject fiber bundle X1 that is usable before the surgery consists of eight nerve fibers, and therefore, the index display 106 determines the functional rate, that is, 80% (8/10) and displays the result as the statistical information of the subject nerve region.

Second Embodiment

The second embodiment is a variant of the first embodiment. The second embodiment differs from the first embodiment in that a medical image processing apparatus 200 in the second embodiment further processes the tumor image in the subject data, so as to determine and display the subject nerve fiber bundles affected by the tumor. Furthermore, in this embodiment, the tumor is taken as an illustrative example of a lesion, and in fact, the lesion may be other situations, such as traumatism, and crassamentum.

An extractor 201, a first converter 202, an analyzer 203, a second converter 204, a display processor 205, and an index display 206 in the medical image processing apparatus 200 of the second embodiment perform additional functions as compared with the extractor 101, the first converter 102, the analyzer 103, the second converter 104, the display processor 105, and the index display 106 of the first embodiment. The following generally illustrates the differences between the second embodiment and the first embodiment, and omits the repeated illustration appropriately.

Figure 7:
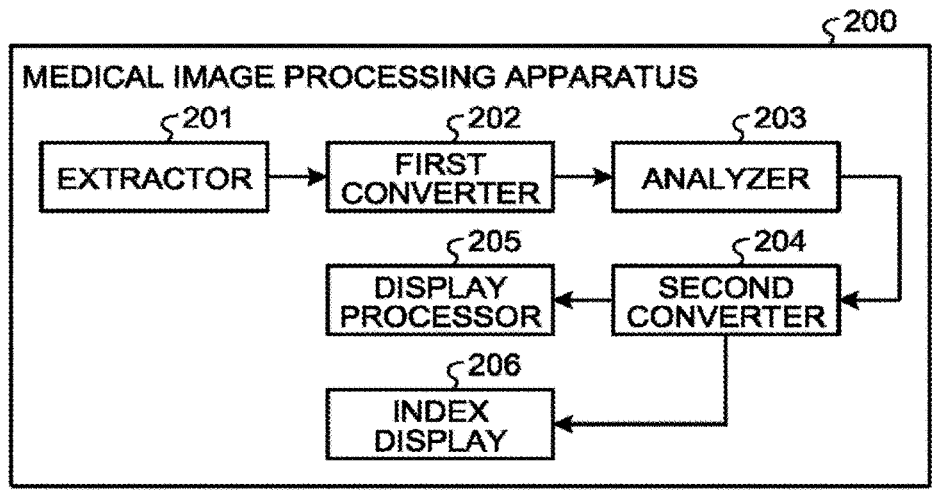
FIG. 7 is a block diagram representing the medical image processing apparatus involved in a second embodiment.

FIG. 7 is a block diagram representing the medical image processing apparatus involved in a second embodiment.

As illustrated in FIG. 7, a medical image processing apparatus 200 comprises: an extractor 201, a first converter 202, an analyzer 203, a second converter 204, a display processor 205, and an index display 206.

The extractor 201 extracts position information of innervation from the subject data, and further extracts information of lesions (such as a tumor region) from the subject data. The subject data further includes a brain image. The brain image may be acquired by imaging the brain of the subject by a medical image diagnostic apparatus such as a magnetic resonance imaging apparatus, an X-ray computed tomography apparatus, an X-ray diagnostic apparatus and a nuclear medicine diagnostic apparatus. If there is a tumor in the brain of the subject, this tumor appears in the brain image. The position of the tumor is denoted as the tumor region.

The first converter 202, as compared with the first converter 102 of the first embodiment, further converts the tumor region contained in the brain image into the fiber bundle atlas in addition to converting the fiber bundle image from the subject into a predefined fiber bundle atlas. The converted tumor region herein may be volumetric data image containing regions within the tumor, and may also be a three-dimensional image of the tumor contour obtained after extracting the tumor contour.

In particular, the first converter 202 first performs the image registration, so as to obtain the conversion matrix between the fiber bundle image of the subject and the fiber bundle atlas. Then, the tumor region of the subject is also converted into the fiber bundle atlas using this conversion matrix. Furthermore, in the second embodiment, as the same with the first embodiment, the first converter 202 may also not convert the fiber bundle image in the subject data into the fiber bundle atlas.

The analyzer 203 analyzes the position relation of the regions of interest in the fiber bundle atlas, the fiber bundles in the fiber bundle atlas and the tumor region converted into the fiber bundle atlas. In particular, the analyzer 203 detects the fiber bundles affected by the tumor region based on the position relation of the fiber bundles in the fiber bundle atlas and the tumor region converted into the fiber bundle atlas to obtain the regions of interest in association with the detected subject fiber bundles based on the correspondence of the regions of interest and the nerve regions having been defined in the fiber bundle atlas, as the analysis result.

The second converter 204 converts the analysis result of the analyzer 203 into the subject data. That is, the regions of interest in association with the detected fiber bundles affected by the tumor region are converted into the subject data.

In addition, the second converter 204 only converts the regions of interest into the subject data, rather than converts the whole fiber bundles affected by the tumor region into the subject data. The reason is that, the global registration of the fiber bundle is very difficult, and as compared with converting the whole fiber bundle, converting only the regions of interest can reduce the difficulty of the registration, the amount of the converted data is less, and the accuracy and efficiency are better.

The display processor 205 displays the subject fiber bundles affected by the tumor region. For example, the analyzer 203 detects the subject fiber bundles affected by the tumor region in the subject data according to the regions of interest converted into the subject data based on the correspondence of the regions of interest and the fiber bundles, and the display processor 205 displays the detected subject fiber bundles. In particular, the analyzer 203 analyses the subject fiber bundles traversing the regions of interest in the subject data with the converted regions of interest, based on the regions of interest and the logical relation therebetween, and thus detects and displays the actual position of the affected subject fiber bundles.

Furthermore, the analyzer 203 can also discriminate functional fiber bundles in the subject data with fiber bundle tracking technique based on the regions of interest corresponding to the functional fiber bundles, and the display processor 205 can display the discriminated functional fiber bundles.

Furthermore, there are multiple ways to display the affected subject fiber bundles. For example, to display the affected subject fiber bundles only, and it may also display all the fiber bundles of the subject and highlight the affected subject fiber bundles.

Figure 8:
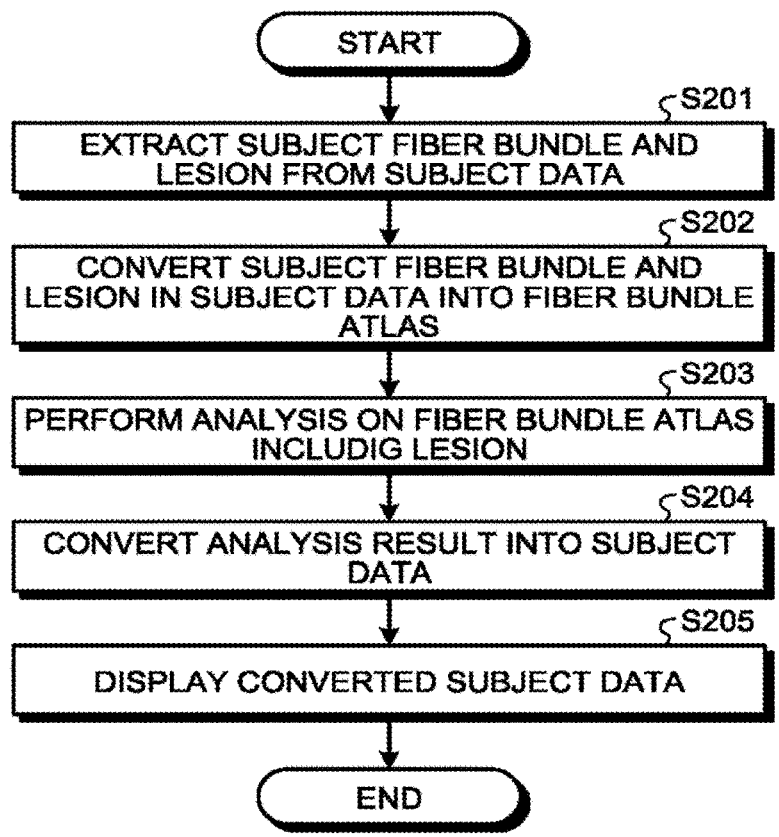
FIG. 8 is a flow chart of image processing steps of the second embodiment.
Figure 9:
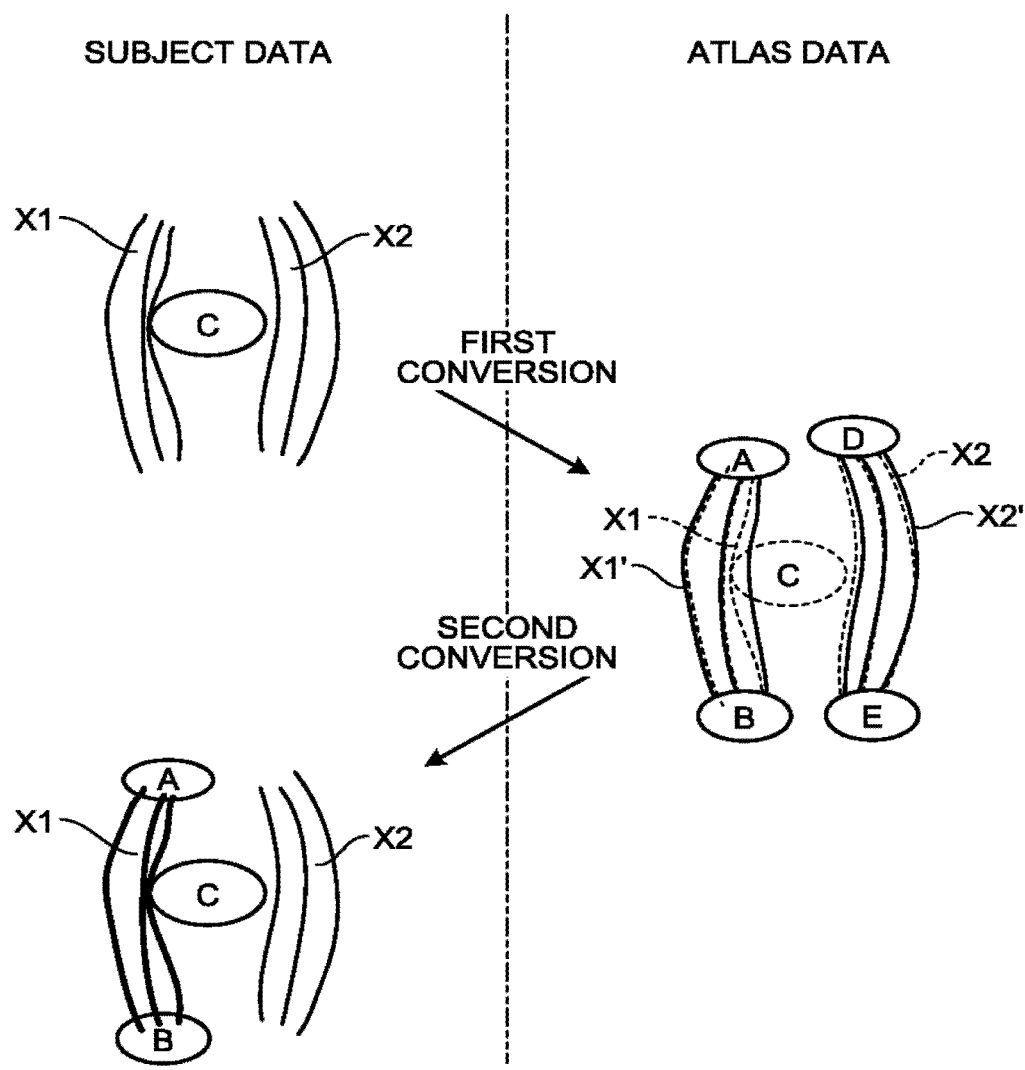
FIG. 9 is a schematic view representing image processing of the second embodiment.

In the following, the image processing process according to the second embodiment is illustrated with reference to FIG. 8 and FIG. 9. FIG. 8 is a flow chart of image processing steps of the second embodiment. FIG. 9 is a schematic view representing image processing of the second embodiment.

First, in step S201, the extractor 201 extracts position information of subject fiber bundles from the subject data, and further extracts position information of the tumor, i.e., tumor region. The upper left of FIG. 8 illustrates a subject fiber bundle X1 and a subject fiber bundle X2 as well as one generally ellipse-shaped tumor region C, the position information of which has been extracted.

In FIG. 8, although the subject fiber bundles X1, X2 and the tumor region C are displayed together for convenience of display, as discussed above, the subject fiber bundles X1, X2 are extracted from the fiber bundle image in the subject data, and the tumor region C is extracted from the brain image of the subject data.

Furthermore, in this embodiment, the tumor region is represented by the tumor contour, and the conversion of the tumor region is conducted.

Next, in step S202, the first converter 202 converts the subject fiber bundles X1, X2 and the tumor region C into the fiber bundle atlas based on the extracted position information.

Before the conversion, the fiber bundle atlas on the right of FIG. 9 contains the fiber bundles X1', X2', and also contains the region of interest A and the region of interest B that correspond to the fiber bundle X1', and the region of interest D and the region of interest E that correspond to the fiber bundle X2'. Fiber bundle X1' consists of three nerve fibers on the left side that are connected between the region of interest A and the region of interest B. Fiber bundle X2' consists of three nerve fibers on the right side that are connected between the region of interest D and the region of interest E.

Furthermore, in step S202, the subject fiber bundles X1, X2 from the subject are converted into the fiber bundle atlas using a conversion matrix obtained by registration, and the tumor region C is converted into the fiber bundle atlas. In FIG. 9, in order to discriminate from the predefined fiber bundles X1', X2', the regions of interest A, B, D, E in the fiber bundle atlas, the subject fiber bundles X1, X2 and tumor region C that are converted into the fiber bundle atlas are represented by dashed lines.

Next, in step S203, the analyzer 203 analyzes the position relation of the regions of interest A, B, D, E in the fiber bundle atlas, the fiber bundles X1', X2' in the fiber bundle atlas, and the tumor region C converted into the fiber bundle atlas. In particular, as the position relation between the fiber bundle X1' or X2' contained in the fiber bundle atlas and the tumor region C that is converted into the fiber bundle atlas illustrates, one of the nerve fibers in the fiber bundle X1' enters the tumor region C and none of fiber bundle X2' enters the tumor region C, and thus the fiber bundle X1' is the fiber bundle affected by the tumor region. Then, based on the correspondence of regions of interest and nerve regions defined in the fiber bundle atlas (in FIG. 9, the correspondence between the fiber bundle X1' and the regions of interest A, B is that the fiber bundle X1' is connected between the regions of interest A, B), the analyzer 203 obtains the region of interest A and the region of interest B corresponding to the detected fiber bundle X1' as the analysis result.

Next, in step S204, the second converter 204 converts the analysis result of the analyzer 203 into the subject data. That is, as illustrated in the lower left of FIG. 9, the region of interest A and the region of interest B corresponding to the detected subject fiber bundle X1' affected by the tumor region are converted into the subject data.

Next, in step S205, the display processor 205 displays the subject data containing the region of interest A and the region of interest B.

In particular, due to the logical relation between the regions of interest A, B and the fiber bundle X1 is that the fiber bundle X1 is connected between the regions of interest A, B, the analyzer 203 derives from the subject data that the fiber bundle connecting the region of interest A and the region of interest B is the subject fiber bundle X1 by using the fiber bundle tracking technique based on the converted regions of interest A, B, and thus detects the actual position of the affected subject fiber bundle X1. Next, the display processor 205 displays the actual position of the detected subject fiber bundle X1.

Here, it is preferred to display in a way that highlights the subject fiber bundle X1 affected by the tumor region C. For example, the subject fiber bundle X1 in FIG. 9 is displayed in bold, and thereby the operator can understand the function division of the fiber bundles more intuitively.

In this embodiment, after the affected functional fiber bundle is determined by the second converter 204, the medical image processing apparatus 200 converts the regions of interest corresponding to this functional fiber bundle into the subject data, and analyses the fiber bundle traversing these regions of interest by the analyzer 203, so as to obtain the actual position of the affected functional fiber bundles in the subject.

By employing this structure, when it is desirable to display the subject fiber bundles affected by the tumor region, it does not need to convert the whole subject fiber bundle in the fiber bundle atlas into the subject data, but only needs to convert the corresponding regions of interest into the subject data, which thus can improve the efficiency and accuracy of the conversion. In addition, if the subject data displays the actual position of the affected functional fiber bundle in the subject, it can facilitate the surgery. By employing the medical image processing apparatus 200 according to the second embodiment, the functional categories of the functional areas corresponding to the nerve fiber bundles can be obtained easily. Moreover, the affected fiber bundles can be accurately determined and the actual positions of the affected fiber bundles in a subject can be accurately and conveniently determined.

In addition, as a variant of the second embodiment, in step S205, the display processor 205 may also not detect and highlight the subject fiber bundle X1, but only display the region of interest A and the region of interest B corresponding to the affected subject fiber bundle X1. By this way, the operator can intuitively observe the regions of interest corresponding to the affected subject fiber bundles, and can also roughly derive the affected subject fiber bundles, and can facilitate the surgery.

Furthermore, the index display 206 of the second embodiment calculates and displays the damage index caused by the tumor region. In the following description, this point is described with reference to FIG. 9.

For example, after the first converter 202 converts the tumor region in the subject data into the fiber bundle atlas, the analyzer 203 analyzes the position relation among the region of interest in the fiber bundle atlas, the nerve region in the fiber bundle atlas, and the tumor region converted into the fiber bundle atlas. For example, as illustrated in the right diagram in FIG. 9, first, the analyzer 203 analyzes the position relation between the fiber bundle X1' or the fiber bundle X2' in the fiber bundle atlas and the converted tumor region C, and thus detects the fiber bundle X1' affected by the tumor region C. Next, the analyzer 203 obtains the region of interest A and the region of interest B corresponding to the detected fiber bundle X1' from the regions of interest A, B, D, E in the fiber bundle atlas based on the correspondence of the regions of interest and the nerve regions having been defined in the fiber bundle atlas.

Next, the analyzer 203 determines the subject nerve region affected by the tumor region based on the obtained functional area. For example, after the region of interest A and the region of interest B are converted into the subject data by the second converter 204, the analyzer 203 detects the subject fiber bundle X1 connecting the region of interest A and the region of interest B from the subject nerve region in the subject data. That is, the analyzer 203 detects the subject fiber bundle X1 with the logical relation similar to the logical relation (connecting the region of interest A and the region of interest B) on the fiber bundle X1' affected by the tumor region.

Next, the index display 206 compares the subject nerve region detected by the analyzer 203 with the nerve region affected by the lesions to calculate the damage index. For example, the index display 206 compares the subject fiber bundle X1 detected by the analyzer 203 with the fiber bundle X1' affected by the tumor region C to calculate statistical information of the subject nerve region as the damage index. In the following, the situation that the tumor region C illustrated in FIG. 9 includes a tumor and the tumor infiltrating area located around the tumor.

For example, the statistical information calculated by the index display 206 is represented by an extrusion rate, a penetrating rate, an infiltration ratio, a damage rate, and a functional rate of a nerve region. For example, the statistical information calculated by the index display 206 is at least one of the extrusion rate, the penetrating rate, the infiltration rate, the damage rate, and the functional rate of a nerve region.

The extrusion rate represents the ratio of the extrusion fiber bundles to the functional fiber bundles related to the regions of interest. As an example, in FIG. 9, one of the nerve fibers in the three fiber bundles X1' traverses the tumor region C. By contrast, the subject fiber bundle X1 does not traverse the tumor region C, and one of the nerve fibers in the fiber bundle X1 has been extruded by the tumor region C and has been shifted toward left. Therefore, the index display 206 calculates the extrusion rate, that is, 33% (1/3) as the statistical information of the subject nerve region.

The penetrating rate represents the ratio of the penetrating fiber bundles to the functional fiber bundles related to the regions of interest. As an example, in FIG. 9, there is no penetrating fiber bundle (a nerve fiber traversing the tumor infiltrating area and the tumor in the subject fiber bundle X1), and therefore, the index display 206 calculates the penetrating rate, that is, 0% (0/3) as the statistical information of the subject nerve region.

The infiltration rate represents the ratio of the infiltration fiber bundles to the functional fiber bundles related to the regions of interest. As an example, in FIG. 9, there is no infiltration fiber bundle (a nerve fiber traversing the tumor infiltrating area but not the tumor in the subject fiber bundle X1), and therefore, the index display 206 calculates the infiltration rate, that is, 0% (0/3) as the statistical information of the subject nerve region.

The damage rate represents the ratio of the functional fiber bundles to be damaged by the surgery to the functional fiber bundles related to the regions of interest. As an example, in FIG. 9, regardless whether the tumor is exclusively resected or the tumor and the tumor infiltrating area are resected, resecting the tumor region C does not damage the nerve fibers in the subject fiber bundle X1, and therefore, the index display 206 calculates the damage rate, that is, 0% (0/3) as the statistical information of the subject nerve region.

As an example, in FIG. 9, the fiber bundle X1' in the fiber bundle atlas consists of three nerve fibers and the subject fiber bundle X1 that is usable before the surgery consists of three nerve fibers, and therefore, the index display 206 calculates the functional rate, that is, 100% (3/3) as the statistical information of the subject nerve region.

Figure 10:
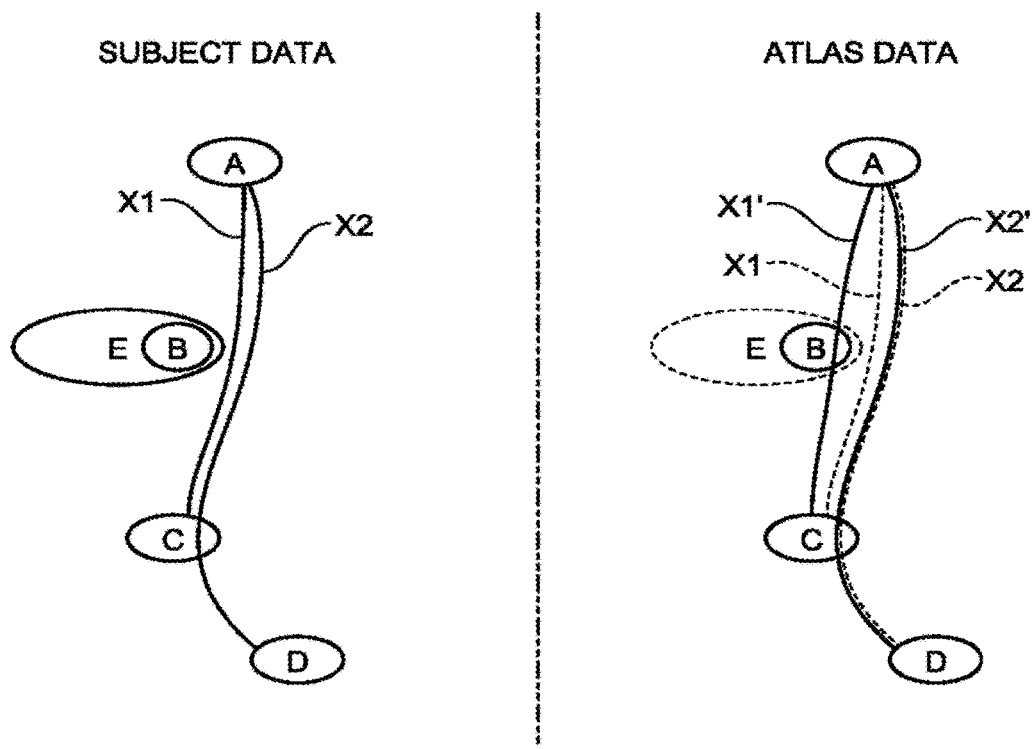
FIG. 10 is a schematic view of determining the affected fiber bundles in case the lesion extrudes the fiber bundles according to a third embodiment.

It is sometimes not able to find the fiber bundles in coincidence with the logical relation of the regions of interest after the regions of interest are converted into the subject data by the second converter 204. For example, as illustrated in FIG. 10, the tumor region shifts the fiber bundles and the region of interest B converted into the subject data exists within the tumor region E. In this case, it can be seen that the fiber bundle X1 is extruded by the tumor region E, and there is no fiber bundle traversing the region of interest B in the tumor region E. However, the functional fiber bundles need to be jointly determined from the regions of interest A, B, C. That is, the affected functional fiber bundle cannot be uniquely determined from the regions of interest A, C located outside the tumor region E only.

The third embodiment is a variant of the second embodiment. The medical image processing apparatus of the third embodiment, which is the same as the medical image processing apparatus of the second embodiment, also comprises: the extractor 201, the first converter 202, the analyzer 203, the second converter 204, the display processor 205, and the index display 206. The following mainly illustrates the differences of the third embodiment and the second embodiment, and the repeated illustration is omitted appropriately.

The differences of these two embodiments is that, in the third embodiment, the analyzer 203 further determines whether there is a region of interest within the tumor region in the subject data, and analyses the actual position of the affected functional fiber bundle by different processing based on the determination.

In case there is no region of interest within the tumor region, by means of the processing of the step S205 in the second embodiment, the actual position of the affected subject fiber bundles can be detected and displayed, and this is not discussed further.

In the following, the situation that there are regions of interest in the tumor region is illustrated with reference to FIG. 10. Here, FIG. 10 is a schematic view of determining the affected functional fiber bundles by converting the region of interest between the subject data and the fiber bundle atlas back and forth in case that the tumor region extrudes the fiber bundles. In the example in FIG. 10, for purpose of illustrating convenience, each fiber bundle contains only one nerve fiber, and the logical relations between the fiber bundles and the regions of interest are all "and".

As illustrated in FIG. 10, in case there is a region of interest B within the tumor region E, the region of interest B is taken as the only region of interest in an internal region of interest (internal functional area), and the region of interest A and region of interest C are taken as the external regions of interest (external functional area). First, in the subject data, the external regions of interest that consists of the region of interest A and the region of interest C is used to determine a first fiber bundle (first nerve region), the first fiber bundle being all the fiber bundles that traverse the external regions of interest and being in coincidence with the logical relations with the region of interest A and the region of interest C (each logical relation in this embodiment is "AND"). The first fiber bundle illustrated in FIG. 10 contains two fiber bundles, which are the subject fiber bundle X1 and the subject fiber bundle X2. Therein, the subject fiber bundle X1 is the fiber bundle extruded by the tumor region E. Next, as illustrated in FIG. 10, in the fiber bundle atlas, the functional fiber bundles that traverse the external regions of interest but not the internal region of interest (the region of interest B) is determined as the second fiber bundle (second nerve region). The second fiber bundle in the fiber bundle atlas illustrated in FIG. 10 that meets the conditions includes one fiber bundle, e.g., fiber bundle X2'. Finally, the first fiber bundle is subtracted by the second fiber bundle to obtain the affected functional fiber bundles (the number of the affected functional fiber bundles illustrated in FIG. 10 is one). That is, the affected fiber bundle (subject fiber bundle X1) can be detected by removing the fiber bundle (subject fiber bundle X2) corresponding to the second fiber bundle (fiber bundle X2') from the first fiber bundle (subject fiber bundle X1, subject fiber bundle X2).

In fact, the fiber bundle X2' in FIG. 10 not only traverse the region of interest A and the region of interest C, but also connects with the region of interest D. In other words, the regions of interest A, C, D are the regions of interest used for uniquely determining this fiber bundle X2'. Therefore, it is needed to convert the regions of interest A, C, D into the subject data while converting the fiber bundle X2' in the second fiber bundle into the subject data. Thus the subject fiber bundles (i.e., the subject fiber bundle X2 illustrated in FIG. 10) that traverse the regions of interest A, C, D and are in coincidence with the logical relation between the regions of interest A, C, D are calculated in the subject data.

FIG. 10 is only an example, the determination methods of the affected functional fiber bubbles will be different as the number of the internal or external regions of interest in the subject data and the number of the functional fiber bundles in the fiber bundle atlas that traverse the external regions of interest are different. However, the variants in coincidence with the gist are all contained in the scope of the embodiments.

Figure 11:
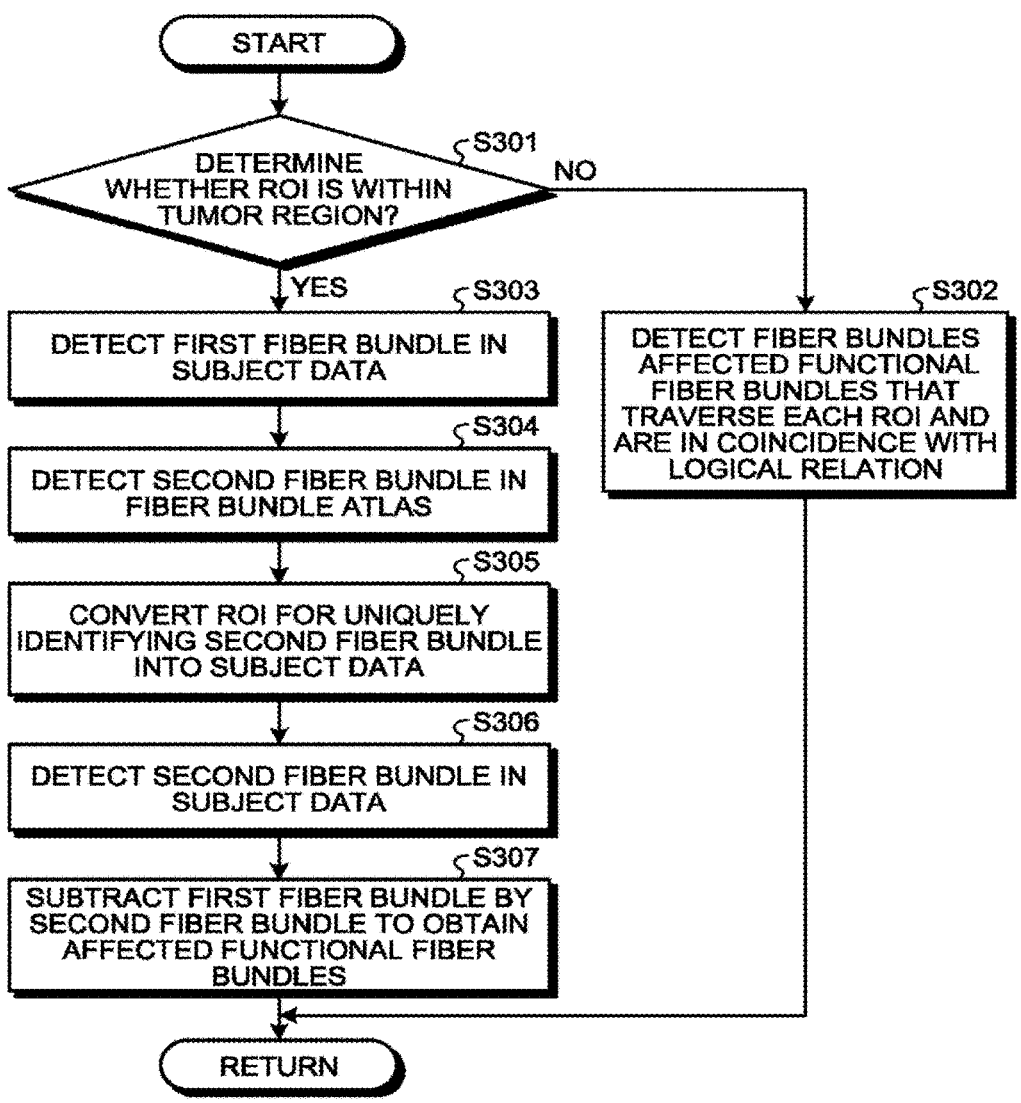
FIG. 11 is a flow chart of image processing steps of the third embodiment.

In the following, the flow chart of the image processing steps involved in the third embodiment is illustrated with reference to FIG. 11. The flow chart in FIG. 11 is a sub-processing of the step S204 in the second embodiment.

The necessary steps in the processing process are illustrated by taking the situation in FIG. 10 as an example.

In step S301, the analyzer 203 determines whether there is a region of interest within the tumor region in the subject data. If it is determined that there is no such a region of interest within the tumor region, the analyzer 203 detects the fiber bundles that traverse the regions of interest and are in coincidence with the logical relation with the regions of interest as the affected functional fiber bundles, and causes the display 205 to display the detected fiber bundles (step S302).

If the analyzer 203 determines there is a region of interest within the tumor region E, the analyzer 203 detects the fiber bundles that traverse the regions of interest of the external regions of interest in the subject data as the first fiber bundle (step S303). In other words, if the analyzer 203 determines there is a region of interest within the tumor region, the analyzer 203 detects the fiber bundles that traverse the regions of interest but not the tumor region in the subject data as the first fiber bundle (step S303).

Next, in step S304, the analyzer 203 detects the functional fiber bundles that traverse the regions of interest of the external regions of interest but not the regions of interest of the internal regions of interest in the fiber bundle atlas as the second fiber bundle, and determines regions of interest for uniquely identifying the fiber bundles for the fiber bundles in the above-mentioned second fiber bundle.

In step S305, the second converter 204 converts the regions of interest determined in the step S304 from the fiber bundle atlas into the subject data.

In step S306, the analyzer 203 derives the fiber bundles that traverse the converted regions of interest and are in coincidence with the logical relation with the regions of interest in the subject data, as the second fiber bundle in the subject data.

In step S307, the analyzer 203 subtracts the first fiber bundle by the second fiber bundle to obtain the affected functional fiber bundles.

According to the medical image processing apparatus of the third embodiment, the actual position of the affected functional fiber bundles can be accurately known and displayed in the case that the tumor region E shifts the fiber bundles and the regions of interest that are converted from the fiber bundle atlas into the subject data are located within the tumor region E.

Furthermore, the index display 206 of the third embodiment calculates and displays the damage index caused by the tumor region. For example, the index display 206 compares the affected functional fiber bundles in the subject data with the affected functional fiber bundles in the fiber bundle atlas to calculate statistical information of the subject nerve region as the damage index. Here, for example, the statistical information calculated by the index display 206 is represented by the extrusion rate, the penetrating rate, the infiltration rate, the damage rate, and the functional rate.

The fourth embodiment is a variant of the second embodiment.

Figure 12:
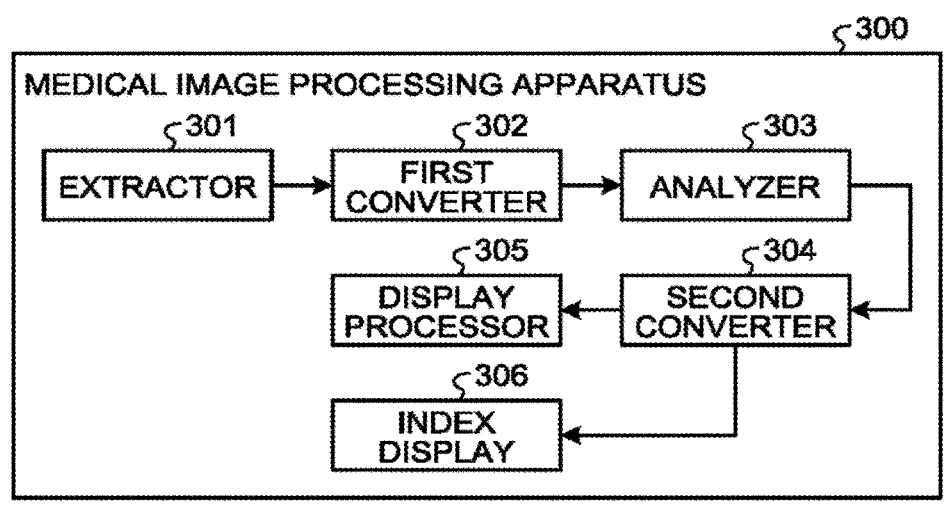
FIG. 12 is a block diagram representing a medical image processing apparatus according to a fourth embodiment.

FIG. 12 is a block diagram representing a medical image processing apparatus according to a fourth embodiment. The fourth embodiment differs from the first embodiment in that a first converter 302, an analyzer 303, a second converter 304, a display processor 305, and an index display 306 perform additional functions as compared with the first converter 102, the analyzer 103, the second converter 104, the display processor 105, and the index display 106 of the first embodiment. The following mainly illustrates the differences of the fourth embodiment and the second embodiment, and omits the repeated illustration appropriately. Furthermore, the tumor region of this embodiment includes the tumor and tumor infiltrating area located around the tumor in FIG. 13.

An extractor 301 extracts position information of innervation and information of the tumor region in the subject data, and further extracts data of regions of interest of the subject obtained from the subject that represents the regions of interest of the subject. For example, the image of functional areas of the subject is acquired by blood oxygen level dependent functional magnetic resonance imaging to extract the data of functional areas of the subject (regions of interest of the subject) in this image.

Figure 13:
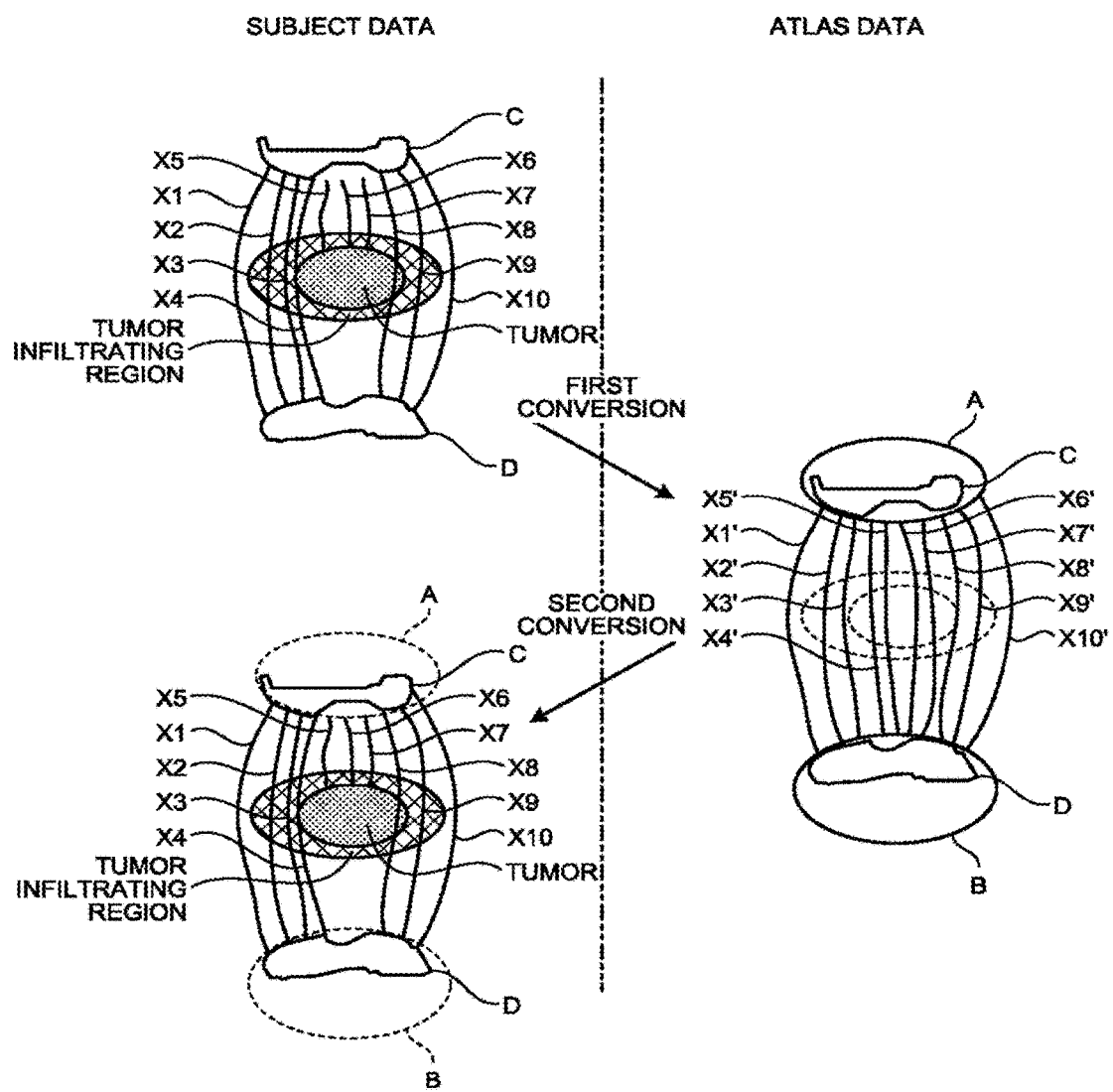
FIG. 13 is a schematic view of analyzing the damage index of the functional fiber bundles according to the fourth embodiment.

The first converter 302 converts the regions of interest of the subject extracted by the extractor 301 into the predefined fiber atlas. FIG. 13 illustrates an example of converting the data of the regions of interest of the subject into the predefined fiber bundle atlas. For purpose of illustrating convenience, only two regions of interest (i.e., the region of interest A and the region of interest B) are illustrated in the fiber bundle atlas of FIG. 13, and it is assumed that the normal situation of the predefined region of interest A and region of interest B appear a generally ellipse-shaped state. FIG. 13 further illustrates two regions of interest (i.e., the region of interest C of the subject and the region of interest D of the subject) of the subject converted into the fiber bundle atlas. In case that a brain tumor occurs, due to the affection of the tumor, not only extrusion, penetrating, infiltration etc. of the functional fiber bundles will occur, and the brain functional areas (regions of interest) will partially (reduce) or even totally disappear. As illustrated in the subject data in FIG. 13, the region of interest C of the subject and the region of interest D of the subject respectively illustrate the cases that the region of interest A and the region of interest B partially disappear due to the affection by the tumor, and the region of interest C of the subject and the region of interest D of the subject turn into an irregular shape from a generally ellipse shape.

The analyzer 303 detects the fiber bundles affected by the tumor region based on the position relation of the fiber bundles in the fiber bundle atlas and the tumor region converted into the fiber bundle atlas, and then obtains the regions of interest corresponding to the detected fiber bundles based on correspondence of the regions of interest defined in the fiber bundle atlas and the fiber bundles as the analysis result. In the example illustrated in FIG. 13, the detected fiber bundles affected by the tumor region are the fiber bundles X1' to X10', the regions of interest that correspond to fiber bundles X1' to X10' are the region of interest A and the region of interest B.

The index display 306 compares the regions of interest of the subject (i.e., actual regions of interest) converted into the fiber bundle atlas with the predefined regions of interest (i.e., the regions of interest in normal situation) in the fiber bundle atlas for the regions of interest affected by the tumor region, to detect the regions of interest that are different from each other as the regions of interest affected by the tumor region.

Furthermore, the index display 306 may further calculate and display the damage index caused by the tumor region based on the comparison. At this point, the damage index caused by the tumor region is a reduction ratio of the regions of interest of the subject with respect to the regions of interest in the atlas data.

Furthermore, the second converter 304 converts the regions of interest in the fiber bundle atlas corresponding to the regions of interest affected by the tumor region into the subject data. The lower left of FIG. 13 illustrates the situation after converting the region of interest A and the region of interest B into the subject data, the two dashed ellipses in this figure represent the contours of predefined region of interest A and region of interest B, respectively.

The index display 306 detects (tracks) the subject fiber bundles in the subject data according to the regions of interest affected by the tumor region, and compares the detected subject fiber bundles in the subject data with the fiber bundles in the atlas data that are affected by the tumor region to calculate the damage index caused by the tumor region.

In the example illustrated in FIG. 13, the subject fiber bundles corresponding to the region of interest A and the region of interest B are tracked base on the position of the tumor region and predefined region of interest A and region of interest B that are converted into the subject data. Ten fiber bundles that are connected between the region of interest A and the region of interest B are illustrated in the subject data of FIG. 13, and there are the fiber bundles X1 to X10 from left to right in the figure.

According to the position relation of the fiber bundles and the tumor in FIG. 13, the fiber bundles X1 to X10 are blocked fiber bundle, infiltration fiber bundle, penetrating fiber bundle, no-affection fiber bundle etc., respectively. The blocked fiber bundle is the fiber bundle blocked by the tumor, the fiber bundle X5, fiber bundle X6 and fiber bundle X7 in FIG. 13 are blocked fiber bundles. The infiltration fiber bundle is the fiber bundle which traverses the tumor infiltrating area located around the tumor but not the tumor, and thus the fiber bundle X2, fiber bundle X3, fiber bundle X4 and fiber bundle X9 in FIG. 13 are infiltration fiber bundles. The penetrating fiber bundle is the fiber bundle that traverses the tumor infiltrating area located around the tumor and the tumor, and thus the fiber bundle X8 in FIG. 13 is a penetrating fiber bundle. No-affection fiber bundle is the fiber bundle that does not traverse the tumor infiltrating area, the fiber bundle X1 and fiber bundle X10 in FIG. 13 are no-affection fiber bundles. In addition, by comparing with the fiber bundle X4' in the fiber bundle atlas of FIG. 13, it can be known that the fiber bundle X4 in the subject data of FIG. 13 have been shifted toward right due to the affection by the tumor position, and the shifted fiber bundle is called the extrusion fiber bundle.

The damage index of the functional fiber bundles can be obtained based on the position of the tracked fiber bundles and the lesions. For example, the damage index is represented by the statistical information of the functional fiber bundles related to the regions of interest, and the statistical information includes at least one of the extrusion rate, penetrating rate, infiltration rate, damage rate, and functional rate.

The extrusion rate represents the ratio of the extrusion fiber bundles to the functional fiber bundles related to the regions of interest. The penetrating rate represents the ratio of the penetrating fiber bundles to the functional fiber bundles related to the regions of interest. The infiltration rate represents the ratio of the infiltration fiber bundles to the functional fiber bundles related to the regions of interest. The damage rate represents the ratio of the functional fiber bundles damaged by the surgery to the functional fiber bundles related to the regions of interest. As the surgical procedures change, the damage rate varies, for example, for the cases of "resecting the tumor only" and "resecting tumor and the tumor infiltrating area", the damage rates are typically different. The functional rate represents the ratio of the functional fiber bundles that are usable before the surgery to the functional fiber bundles related to the regions of interest.

Table 1 represents the statistical information of the subject fiber bundles in FIG. 13. For example, the index display 306 calculates and displays each piece of the statistical information represented in Table 1.

| statistical information | statistical value | statistical related fiber |
|---|---|---|
| extrusion rate | $1/10 = 10\%$ | X4 |
| penetrating rate | $1/10 = 10\%$ | X8 |
| infiltration rate | $4/10 = 40\%$ | X2, X3, X4, X9 |
| damage rate (resecting the tumor only) | $1/10 = 10\%$ | X8 |
| damage rate (resecting tumor and the tumor infiltrating area) | $5/10 = 50\%$ | X2, X3, X4, X8, X9 |
| functional rate | $7/10 = 70\%$ | X1, X2, X3, X4, X8, X9, X10 |

Figure 14:
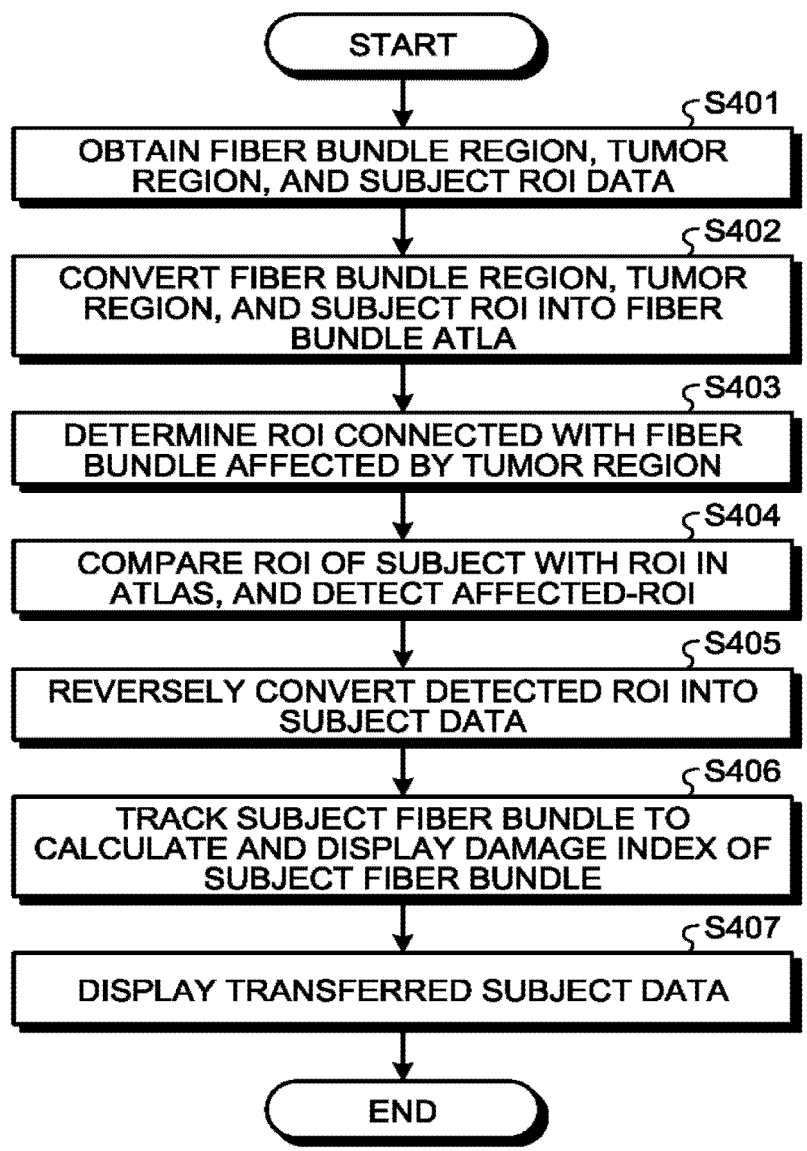
FIG. 14 is a flow chart of image processing steps of the fourth embodiment.

In the following, the flow of the image processing steps of the fourth embodiment is illustrated with reference to FIG. 14.

First, in step S401, in addition to the position information of innervation and the information of the tumor region, the data of regions of interest of the subject obtained from the subject that represents the regions of interest of the subject is extracted.

In step S402, in addition to converting the fiber bundle image and the lesions image into the predefined fiber bundle atlas, the first converter 302 further converts the data of regions of interest of the subject extracted by the extractor 301 into the predefined fiber atlas using a conversion matrix.

In step S403, the analyzer 303 determines the regions of interest connected with the fiber bundles affected by the tumor region.

In step S404, the index display 306 compares the regions of interest (i.e., actual regions of interest) of the subject converted into the fiber bundle atlas with the predefined regions of interest (i.e., the regions of interest in normal situation) in the fiber bundle atlas for the regions of interest determined in step S403, and detects the regions of interest that are different between the two situations as the regions of interest affected by the tumor region.

In step S405, the second converter 304 converts the regions of interest in the fiber bundle atlas corresponding to the regions of interest affected by the tumor region into the subject data.

In step S406, the index display 306 detects (tracks) the subject fiber bundles in the subject data according to the regions of interest affected by the tumor region, and compare the detected subject fiber bundles in the subject data with the fiber bundles in the atlas data that are affected by the tumor region to calculate and display the damage index caused by the tumor region. The damage index caused by the tumor region is represented by the statistical information of the subject fiber bundle, and the statistical information is at least one of the extrusion rate, the penetrating rate, the infiltration rate, the damage rate, and the functional rate.

In step S407, the display processor 305 further displays the converted subject data.

Figure 15:
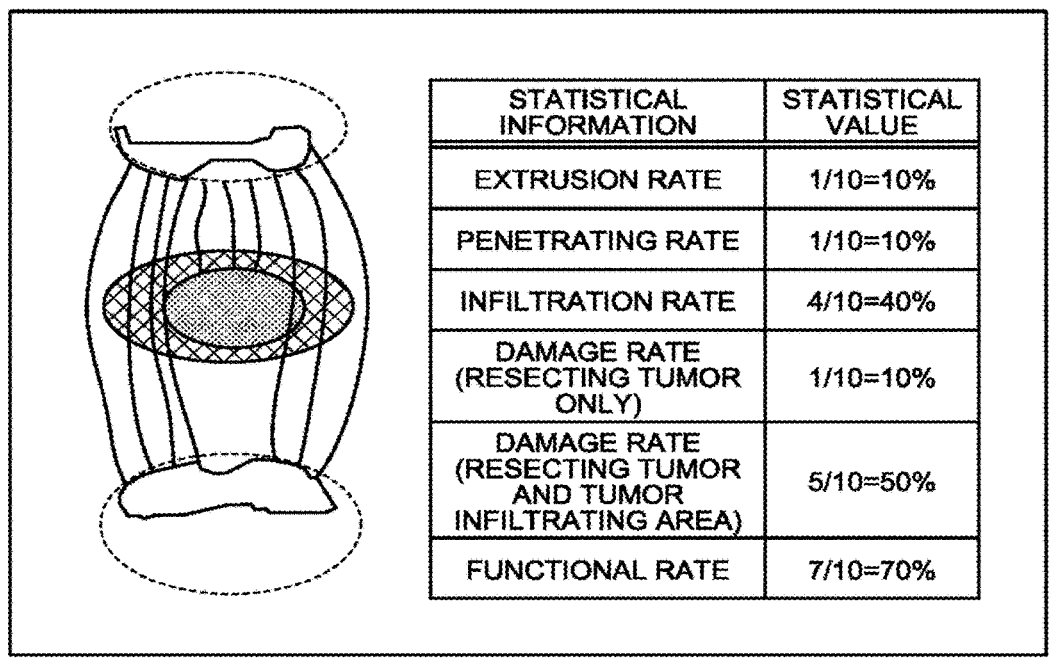
FIG. 15 is a schematic view of a picture that displays the damage index and the subject data simultaneously.

FIG. 15 illustrates the schematic view after the display of the index display 306 and the display processor 305.

Furthermore, as a variant of this embodiment, in step S404, the reduction ratio of the regions of interest of the subject with respect to the regions of interest in the atlas data can also be calculated and displayed as the damage index caused by the tumor region. At this point, it is also possible to omit step S406 and do not calculate the statistical information of the subject fiber bundles.

In this embodiment, a medical image processing apparatus 300 converts the predefined regions of interest in normal situation into the subject data to track the functional fiber bundle in the subject data, so that it is possible to intuitively determine the damage degree of the functional fiber bundles. By employing such constitution, the problem that the subject fiber bundles corresponding to the regions of interest cannot be accurately tracked in the subject data due to partially or totally disappearing of the brain functional areas can be avoided. This is because the reduction of the regions of interest, tracking the number of the fiber bundles based on such regions of interest may smaller than the actual number of the fiber bundles that should be tracked.

Furthermore, based on the predefined regions of interest in normal situation and the position of the tumor, the functional fiber bundles can be divided into blocked fiber bundle, infiltration fiber bundle, penetrating fiber bundle, no-affection fiber bundle etc.; and the damage degree of the functional fiber bundles can be intuitively displayed though the statistical information (for example, at least one of the extrusion rate, the penetrating rate, the infiltration rate, the damage rate, and the functional rate) of the functional fiber bundles related to the regions of interest based on the relation of the actual position of the functional fiber bundles of the subject and the tumor position.

The medical image processing apparatus of the embodiments can also be installed in the medical device as processing circuitry capable of implementing the functions illustrated in various embodiments, and may also be provided as programs executable by a computer, stored in the storage mediums such as disks (soft disk (floppy, registered trademark), hard disk, etc.), compact discs (CD-ROM, DVD, etc.), photo magneto disks (MO) and semiconductor memory to issue.

Also, the MW (Middleware) such as OS (Operation System), database management software and network software, running on a computer based on the instructions of the programs installed from the storage mediums to the computer, can also perform a portion of the processing for implementing the above embodiments.

By employing at least one of the embodiments, the functional categories of the functional areas corresponding to the nerve fiber bundles can be obtained easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising processing circuitry configured to:
   extract position information of innervation from subject data;
   convert a subject nerve region that is based on the extracted position information into atlas data;
   analyze a position relation between a functional area in a brain in the atlas data and the converted subject nerve region; and
   convert the analysis result into the subject data.

2. The medical image processing apparatus according to claim 1, wherein the processing circuitry is configured to
   obtain the functional area corresponding to the converted subject nerve region as the analysis result,
   obtain the nerve region in association with the obtained functional area based on a correspondence of the functional area and the nerve region defined in the atlas data, and
   compare the converted subject nerve region with the obtained nerve region to calculate and display a damage index.

3. The medical image processing apparatus according to claim 2, wherein
   the damage index includes statistical information of the subject nerve region, and
   the statistical information is a functional rate of the nerve region.

4. The medical image processing apparatus according to claim 2, wherein,
   the nerve region is a region corresponding to a nerve fiber bundle, and
   the functional area is a region corresponding to a brain function or a region corresponding to a tissue structure in the brain.

5. The medical image processing apparatus according to claim 1, wherein the processing circuitry is configured to
   extract position information of a lesion,
   convert a tumor region that is based on the extracted position information of the tumor into the atlas data, and
   analyze the position relation between the functional area in the atlas data, the nerve region in the atlas data and the converted tumor region.

6. The medical image processing apparatus according to claim 5, wherein the processing circuitry is configured to
   detect the nerve region affected by the lesion based on the position relation between the nerve region and the converted tumor region, and
   obtain the functional area in association with the detected nerve region based on a correspondence of the functional area and the nerve region defined in the atlas data, as the analysis result.

7. The medical image processing apparatus according to claim 6, wherein the processing circuitry is configured to
   detect the subject nerve region affected by the lesion based on the obtained functional area, and
   display the detected subject nerve region.

8. The medical image processing apparatus according to claim 7, wherein the processing circuitry is configured to display an image highlighting the subject nerve region affected by the lesion.

9. The medical image processing apparatus according to claim 7, wherein
   one nerve region is associated with multiple functional areas in the atlas data,
   when at least one of the functional areas locates in the lesion, the processing circuitry is configured to
      detect the subject nerve region as a first nerve region that traverses an external functional area excluding an internal functional area located in the lesion in the functional areas,
      detect the nerve region as a second nerve region that traverses the external functional area but not the internal functional area, and
      detect the subject nerve region affected by the lesion by removing the subjected nerve region corresponding to the second nerve region from the first nerve region.

10. The medical image processing apparatus according to claim 7, wherein the processing circuitry is configured to compare the detected subject nerve region with the nerve region affected by the lesion to calculate and display a damage index caused by the lesion.

11. The medical image processing apparatus according to claim 10, wherein
    the damage index includes the statistical information of the subject nerve region, and
    the statistical information is at least one of an extrusion rate, an penetrating rate, an infiltration rate, a damage rate, and a functional rate of the nerve region.

12. The medical image processing apparatus according to claim 6, wherein the processing circuitry is configured to
    extract position information of a functional area in a brain from the subject data,
    convert the subject functional area that is based on the extracted functional area into the atlas data, and
    compare the obtained functional area with the converted subject functional area to calculate and display a damage index caused by the lesion.

13. The medical image processing apparatus according to claim 12, wherein the damage index is a reduction ratio of the subject functional area with respect to the functional area in the atlas data.

14. The medical image processing apparatus according to claim 12, wherein the processing circuitry is configured to
    detect the subject nerve region affected by the lesion based on the functional area in association with the detected nerve region, and
    compare the detected subject nerve region with the nerve region affected by the lesion to calculate and display the damage index caused by the lesion.

15. The medical image processing apparatus according to claim 14, wherein
    the damage index includes the statistical information of the subject nerve region, and the statistical information is at least one of an extrusion rate, an penetrating rate, an infiltration rate, a damage rate, and a functional rate of the nerve region.

16. A medical image processing method, comprising:

extracting position information of innervation from subject data;

converting a subject nerve region that is based on the extracted position information into atlas data;

analyzing a position relation between a functional area in a brain in the atlas data and the converted subject nerve region; and converting the analysis result into the subject data.

* * * * *